(12) United States Patent
Lin (10) Patent No.: US 10,130,676 B2
(45) Date of Patent: Nov. 20, 2018

(54) THERAPEUTIC PEPTIDES FOR CEREBROVASCULAR DISEASES

(71) Applicant: Prime Bio-Drug Development Limited, Road Town, Tortola (VG)

(72) Inventor: Chen-Lung Lin, Taiwan (CN)

(73) Assignee: Prime Bio-Drug Development Limited, Tortola (VG)

( * ) Notice: Subject to any disclaimer, the term of this patent is extended or adjusted under 35 U.S.C. 154(b) by 0 days.

(21) Appl. No.: 15/566,937

(22) PCT Filed: Apr. 16, 2015

(86) PCT No.: PCT/CN2015/076747
§ 371 (c)(1),
(2) Date: Oct. 16, 2017

(87) PCT Pub. No.: WO2016/165102
PCT Pub. Date: Oct. 20, 2016

(65) Prior Publication Data
US 2018/0125923 A1    May 10, 2018

(51) Int. Cl.
| | |
|---|---|
| *A61K 38/00* | (2006.01) |
| *A61K 38/10* | (2006.01) |
| *C07H 21/00* | (2006.01) |
| *C07K 14/47* | (2006.01) |
| *A61P 9/10* | (2006.01) |
| *A61K 38/08* | (2006.01) |
| *C07K 7/06* | (2006.01) |
| *C07K 7/08* | (2006.01) |

(52) U.S. Cl.
CPC .............. *A61K 38/10* (2013.01); *A61K 38/08* (2013.01); *A61P 9/10* (2018.01); *C07H 21/00* (2013.01); *C07K 7/06* (2013.01); *C07K 7/08* (2013.01); *C07K 14/47* (2013.01); *A61K 38/00* (2013.01)

(58) Field of Classification Search
None
See application file for complete search history.

(56) References Cited

U.S. PATENT DOCUMENTS

2003/0077266 A1    4/2003  Lezdey et al.

FOREIGN PATENT DOCUMENTS

| | | |
|---|---|---|
| CN | 104321337 A | 1/2015 |
| WO | 2013/173941 A1 | 11/2013 |

OTHER PUBLICATIONS

Moldthan et al. (J Stroke Cerebrovasc Dis. 2014 ; 23(5): e355-e363. doi:10.1016/j.jstrokecerebrovasdis.2013.12.029).*
Patent Cooperation Treaty, International Search Report for International Application No. PCT/CN2015/076747 dated Jan. 22, 2016, 6 pages.
Patent Cooperation Treaty, Written Opinion of the International Searching Authority for International Application No. PCT/CN2015/076747 dated Jan. 22, 2016, 5 pages.
Moldthan, Huang L., et al., "Alpha 1-antitrypsin therapy mitigated ischemic stroke damage in rats," Journal of Stroke and Cerebrovascular Diseases, Jun. 30, 2014, vol. 23, Issue No. 5, pp. e355-e363.
Greene, Lloyd A., and Tischler, Arthur S., "Establishment of a noradrenergic clonal line of rat adrenal pheochromocytoma cells which respond to nerve growth factor," Proceedings of the National Academy of Sciences of the United States of America, vol. 73, No. 7, Jul. 1976, pp. 2424-2428.
Jiang, Bin, et al., "Incidence and Trends of Stroke and Its Subtypes in China: Results from Three Large Cities," Stroke, Jan. 2006, vol. 37, pp. 63-68, originally published online Nov. 23, 2005.
Khan, Shaheen, et al., "Cobaltous Chloride and Hypoxia Inhibit Aryl Hydrocarbon Receptor-Mediated Responses in Breast Cancer Cells," Toxicology and Applied Pharmacology, Aug. 15, 2007, vol. 223, No. 1, 28-38, 20 pages.
Magistretti, Pierre J., "Cellular bases of functional brain imaging: insights from neuron-glia metabolic coupling," Brain Research, 2000, vol. 886, pp. 108-112.
Manev, Hari, et al., "Delayed Increase of CA2+ Influx Elicited by Glutamate: Role in Neuronal Death," Molecular Pharmacology, 1989, vol. 36, pp. 106-112.
Nedergaard, Maiken, et al., "Acid-induced Death in Neurons and Glia," The Journal of Neuroscience, Aug. 1991, vol. 11, No. 8, pp. 2489-2497.

* cited by examiner

*Primary Examiner* — Jeanette M Lieb
(74) *Attorney, Agent, or Firm* — Fitch, Even, Tabin & Flannery, LLP (57) ABSTRACT

The present invention provides a method for treating or ameliorating cerebrovascular diseases in a subject by using peptides isolated from extracts from rabbit skin inflamed by vaccinia virus. The present invention also provides a peptide comprising an amino acid sequence having at least 70% identity to SEQ ID NO: 1, or variants, mutants, derivatives, or fragments thereof.

12 Claims, 10 Drawing Sheets

Specification includes a Sequence Listing.

Fig 1. Schematic representation of the procedures used for screening polypeptide/small peptide-level analgesic agents from crude extracts of the inflamed rabbit skins induced by inoculation of vaccinia virus.

Fig 2. Identification of functional peptide.

Fig 3. The stability of peptide-5 in environments of various pH values.

Figure 4: MALDI-TOF MS spectra of the samples

Fig 5. CD of peptide 5

Fig 6. Cell survival of the PC12 cells exposed to $H_2O_2$ for 24h, with or without treatment by AGC 0.25, 0.5, or 1 U/ml. ** $P<0.01$ compared with no treatment. Data are expressed as mean ± SD from 3 experiments.

Fig 7. Cell survival of the PC12 cells exposed to $H_2O_2$ for 24h, with or without treatment by AGC 1 U/ml, or peptide 1 (10 µg/ml), peptide 5 (10 µg/ml) or in combination of peptide 1 and 5 (10 µg/ml each). ** $P<0.05$ compared with individual use of peptide 1 or 5. Data are expressed as mean ± SD from 3 experiments.

Figure 8: Effect of AGC on the Cell Survival of L-Glutamic-acid Treated PC12 Cells Figure 9: Comparison between the Effect of AGC, Peptide 1, and Peptide 5 on Cell Survival of L-Glutamic-acid Treated PC12 Cells Fig 10. Cell survival of the PC12 cells under conditions of hypoglycemic, hypoxic or a combination of both for 24h, with or without treatment by AGC 0.25, 0.5 or 1 U/ml. ** $P<0.01$ compared with no treatment. Data are expressed as mean ± SD from 3 experiments.

Fig 11. Cell survival of the PC12 cells under conditions of hypoglycemic, hypoxic or a combination of both for 24h, with or without treatment by AGC 1 U/ml, or peptide 1 (10 µg/ml), peptide 5 (10 µg/ml) or in combination of peptide 1 and 5 (10 µg/ml each). ** $P<0.01$ compared with individual use of peptide 1 or 5. Data are expressed as mean ± SD from 4 experiments.

Fig 12. Injection of peptide 1 and 5 resulted in high fluorescent intensity detected in the brain (shown in yellow) in 15 and 30 minutes (left and right rat), whereas injection of control peptide did not (middle). Data are representative of 3 experiments.

Fig 13. Injection of peptide 1 and 5 resulted in high fluorescent intensity detected in the spinal cord (shown in yellow) in 30 and 60 minutes (left and right rats), whereas injection of control peptide did not (middle). Data are representative of 3 experiments.

SEQUENCE LISTING

```
<160> NUMBER OF SEQ ID NOS: 2

<210> SEQ ID NO 1
<211> LENGTH: 11
<212> TYPE: PRT
<213> ORGANISM: Unknown
<220> FEATURE:
<223> OTHER INFORMATION: SYNTHESIZED

<400> SEQUENCE: 1

Asp Glu Ala Gln Glu Thr Ala Val Ser Ser His
1               5                   10

<210> SEQ ID NO 2
<211> LENGTH: 14
<212> TYPE: PRT
<213> ORGANISM: Unknown
<220> FEATURE:
<223> OTHER INFORMATION: SYNTHESIZED

<400> SEQUENCE: 2

Asp Glu Ala Gln Glu Thr Ala Val Ser Ser His Glu Gln Asp
1               5                   10
```

THERAPEUTIC PEPTIDES FOR CEREBROVASCULAR DISEASES

CROSS-REFERENCE TO RELATED APPLICATION

This application is a U.S. national phase application filed under 35 U.S.C. § 371 of International Application Number PCT/CN2015/076747, filed Apr. 16, 2015, designating the United States.

REFERENCE TO A SEQUENCE LISTING

The Sequence Listing associated with this application is filed in electronic format via EFS-Web and is hereby incorporated into the specification in its entirety. The name of the text file containing the Sequence Listing is "FPCH14160101_US_171122_CORRECTED_SEQUENCE_LISTING." The size of the text file is 4.0 KB, and the text file was created on Nov. 22, 2017.

FIELD OF THE INVENTION

The present invention relates to the treatment of cerebrovascular diseases. In particular, it relates to a method for treating or ameliorating cerebrovascular diseases in a subject by using peptides isolated from extracts from rabbit skin inflamed by vaccinia virus.

BACKGROUND OF THE INVENTION

Cerebrovascular diseases are neural function injuries caused by abnormal blood supply of regional brain. In most countries, cerebrovascular diseases, the top three causes of all deaths, can result in a brain injury in adult. Cerebrovascular disease is a major cause for endangering the health of the middle-aged and the aged people, and a major cause of death or disability of the middle-aged and the aged people in most countries.

Stroke, one of the acute cerebrovascular diseases, is the third leading cause of death in worldwide population and induces a highest disabling rate among various diseases. The cerebrovascular diseases could severely affect the life quality of the elderly, bring an enormous burden to patients' family and the society. It also tends to increase in young population.

The cerebrovascular diseases are primarily classified into two types, hemorrhagic and ischemic, of which the latter is 60-70%, and is the most common type of cerebrovascular diseases. It is important to study the pathophysiological mechanism of ischemic cerebrovascular diseases and search for drugs which function as neuroprotection.

The research of the pathophysiologic mechanism of cerebral ischemia has been one of the most focuses of the neuroscience field since 1980s, and so far theories of cerebral ischemia concerning such as energy metabolism, acid intoxication, peroxidation injury, excitatory amino acid induced toxicity injury and calcium overload have been proposed, in which the last two play an important role in ischemic neuronal injury and death. According to pathophysiologic basis of ischemic cerebrovascular diseases, drugs currently used to clinically treat cerebral ischemia mainly comprise calcium ion antagonists (nimodipine), oxygen radical scavengers (VitE, SOD), neurotrophic factors (nerve growth factor, neurotrophic factor), excitatory amino acid antagonists, antioxidants and drugs which improve late-onset neuronal injury. These drugs function via various mechanisms of action, with uncertain therapeutical effects or less specificity or with the concomitancy of severe side-effects, and thus can not meet the clinical requirements yet. There are many commercially available drugs which can be used to improve cerebral circulation, metabolism and functions, such as piracetam, flunarizine, calan, ginkgo extracts. Although they all have certain characteristics, the treatment effects thereof on cerebrovascular diseases are uncertain. Research and development of novel drugs for treating ischemic cerebrovascular diseases becomes increasingly important in the field of pharmaceutics and pharmacology.

The extracts from rabbit skin inflamed by vaccinia virus are commercially available, with the trade name of analgecine, which is manufactured by Vanworld Pharmaceutical (Rugao) Co. Ltd. Previous experiment evidence shows that crude extract of the inflammatory rabbit skins induced by inoculation of vaccinia virus can exert its pharmacological effect on analgesia. However, the active ingredients of analgecine contributing to this effect have not been reported yet. Therefore, there is a need to gain an insight into which components are involved in this effect.

SUMMARY OF THE INVENTION

In one aspect, the present invention provides a method for treating or ameliorating cerebrovascular diseases in a subject, wherein the method comprises administering to the subject an effective amount of one or more peptide comprising an amino acid sequence having at least 70% identity to DEAQETAVSSH (SEQ ID NO: 1) or variants, mutants, derivatives, or fragments thereof.

In another aspect, the present invention provides the use of one or more peptide comprising an amino acid sequence having at least 70% identity to SEQ ID NO: 1 or variants, mutants, derivatives, or fragments thereof in the manufacture of a medicament for treating cerebrovascular diseases in a subject.

In one embodiment, the cerebrovascular diseases as described herein are those which lead to damages of the neurological systems with functional deficit. In a particular embodiment, the cerebrovascular diseases as described herein are selected from the group consisting of: ischemic brain injury or hemorrhage brain damage. In a more particular embodiment, the cerebrovascular disease is stroke.

The expression "having at least 70% identity to SEQ ID NO: 1" is intended to mean an amino acid sequence having at least 75%, 80%, 85%, 90%, 95%, 98% or 99% or more identity to SEQ ID NO: 1.

In a further embodiment, wherein the peptide comprises SEQ ID NO: 1 and/or DEAQETAVSSHEQD (SEQ ID NO: 2). In a more particular embodiment, the peptide consists of SEQ ID NO: 1 and/or SEQ ID NO: 2.

In various embodiments, the peptide comprises at least one amino acid addition, deletion, and/or substitution, preferably 1-5, preferably 1-3 amino acid additions, deletions, and/or substitutions. In another embodiment, the amino acid addition, deletion and/or substitution are located at the C-terminal and/or N-terminal.

In yet another embodiment, the disease is treated or ameliorated by protecting nerve cells.

In a particular embodiment, the subject is human.

In another aspect, the present invention relates to a polynucleotide which encodes the peptide according to the invention; a vector which comprises such polynucleotide; as well as a host cell which comprises such polynucleotide or such vector.

In another aspect, a pharmaceutical composition is provided comprising an effective amount of the peptide according to the invention, the polynucleotide, the vector, or the host cell as described herein, and a pharmaceutically acceptable carrier.

The present invention also relates to the peptide, the polynucleotide, the vector, the host cell, or the pharmaceutical composition as described herein, for use as a medicament. In particular, the present invention relates to a peptide composition comprising or consisting of SEQ ID NO: 1 and SEQ ID NO: 2; a drug combination comprising such a composition; as well as a method of using the same.

DETAILED DESCRIPTION

The present inventors surprisingly found that 2 peptides isolated from extracts from rabbit skin inflamed by vaccinia virus significantly preserve the neural cell viability under hypoxic, hypoglycemia conditions or a combination of both, upon exposure to $H_2O_2$ or L-glutamic acid in vitro and/or in vivo. More surprisingly, the peptide 1 and peptide 5 exhibit synergistic effects to inhibit cytotoxicity of neuronal cell (PC12) induced by hypoxic, hypoglycemia conditions or a combination of both, $H_2O_2$ and L-glutamic acid, with a similar potency as seen in the use of AGC (eg, 1 U/ml). Our data therefore successfully identify two short peptides in the AGC as active ingredients that could account, at least in part, for the neuro-protective role of AGC in the ischemic stroke.

$H_2O_2$ is an important reactive oxygen component which is involved in the onset of nervous system diseases such as cerebral ischemia, trauma, brain aging, Alzheimer's disease etc. It will peroxidize the membrane lipid, decrease cell membrane fluidity, change components and activities of intracellular proteins, make chromatin concentrated and DNA broken, and finally result in cell death.

Excitatory amino acids, such as glutamic acids, play an important role in the course of a variety of chronic or acute neuropathy which will be accompanied by neuronal death. Glutamic acid can damage nerve cell line and primary nerve cell in a dose dependent manner. It is responsible for the increased intracellular calcium ion and the blocked cystine uptake, and it induces the loss of intracellular reduced glutathione (GSH), the increased oxygen radical and nerve cell death. Therefore, $H_2O_2$ or glutamic acid-induced nerve cell injury model can be used as a screening model of neuroprotective agents.

Therefore, in one embodiment, the peptide according to the invention is used to preserve the neural cell viability upon exposure to $H_2O_2$ in vitro and/or in vivo, with an unexpected synergistic effect seen in the combinatorial use of peptide 1 and 5. In another embodiment, the peptide according to the invention demonstrates protective effect on the L-glutamic-acid-treated PC12 cells, with an unexpected synergistic effect seen in the combinatorial use of peptide 1 and 5

Neuronal activity requires a continuous supply of oxygen and glucose. The impairment of oxidative metabolism causes a cascade of ionic and metabolic events leading to neuronal death. Therefore, in one embodiment, the peptide according to the invention is used to preserve the neural cell viability under hypoglycemic and hypoxic conditions in vitro and/or in vivo, with an unexpected synergistic effect seen in the combinatorial use of peptide 1 and 5.

In one embodiment, the present invention relates to a method for preserving the neural cell viability upon exposure to $H_2O_2$ in vitro or in vivo, comprising treating the neural cell with peptide 1 and/or 5 or administering peptide 1 and/or 5 to the subject in need thereof.

In another embodiment, the present invention relates to a method for preserving the neural cell viability under hypoglycemic and/or hypoxic conditions in vitro or in vivo, comprising treating the neural cell with peptide 1 and/or 5 or administering peptide 1 and/or 5 to the subject in need thereof.

In yet another embodiment, the present invention relates to a method for protecting the neural cell from glutamic acid-induced injury in vitro or in vivo, comprising treating the neural cell with peptide 1 and/or 5 or administering peptide 1 and/or 5 to the subject in need thereof.

Unless defined otherwise, all scientific terms used herein have the same meaning as that commonly understood by one of ordinary skill in the art. Exemplary methods and materials are described below, although the equivalents thereof can be used. All publications and other references mentioned herein are incorporated by reference in their entirety.

The present invention will now be described further with reference to the following examples which, however, are not intended to limit the scope of the present invention.

Example 1 Isolation and Characterization of Active Ingredients in Analgecine) (AGC)

1.1. Isolation of Analgecine Active Ingredients and Structural Analysis
1.1.1. Materials and Methods
1) Sample Preparation About 200 µL of the mixture of biological agents generated from the rabbit skin suffering from inflammation induced by inoculation of vaccinia virus was dried in a vacuum centrifuge.

The lyophilized material was reconstituted with 100 µL of 0.5 M ammonia bicarbonate buffer (pH 8.5) containing 8 M urea and 0.5 M dithiothreitol (DTT) for 1 hr at 37° C., and for another 2 hr at 4° C. under dark condition when 10 μL of 0.5 M iodoacetamide (IAM) was added for alkylation prior to dilution with 400 μL ammonium bicarbonate. Subsequently, the resulting solutions were then digested with 0.2 μg of trypsin for 18 h at 37° C., and then the trypsin-digested solutions were acidified by 10% trifluoroacetic acid (TFA)/$H_2O$ to pH 3.0 value. After the reaction, the totally acidified solutions were applied onto the reverse phase C18 column pre-equilibrated with 200 L of 0.1% TFA/$H_2O$ (pH 3.0). The column was also washed with 200 μL of 0.1% TFA/$H_2O$ (pH 3.0) and then eluted with a stepwise acetonitrile gradient from 50% to 100% in 0.1% TFA at room temperature. As a control in nano-LC-MS/MS, the reconstituted liquid from lyophilized products was also treated by reduction, alkylation, desalting and acidified as mentioned above, except for trypsin digestion.

2) Nano-LC-MS/MS Analysis

The eluted fractions were collected, dried in a vacuum centrifuge, and then reconstituted in 25 μL of 80% ACN in $H_2O$ and analyzed by LTQ Orbitrap XL (Thermo Fisher Scientific, San Jose, Calif.). Reverse phase nano-LC separation was performed on an Agilent 1200 series nanoflow system (Agilent Technologies, Santa Clara, Calif.). A total of 10 μL sample from fraction was loaded onto an Agilent Zorbax XDB C18 precolumn (0.35 mm, 5 μm), followed by separation using a C18 column (i.d. 75 μm×25-cm, 3 μm, Micro Tech, Fontana, Calif.). The mobile phases used were (A) 0.1% FA and (B) 0.1% FA in 100% ACN. A linear gradient from 5% to 35% (B) over a 90-min period at a flow rate of 300 nL/min was applied. The peptides were analyzed in the positive ion mode by applying a voltage of 1.8 Kv to the injection needle. The MS was operated in a data-dependent mode, in which one full scan with m/z 300-2000 in the Orbitrap (R=60 000 at m/z 400) using a rate of 30 ms/scan. The six most intense peaks for fragmentation with a normalized collision energy value of 35% in the LTQ were selected. A repeat duration of 30 s was applied to exclude the same m/z ions from the reselection for fragmentation.

3) Database Search and Identification

Peptides were identified by peak lists converted from the nanoLC-MS/MS spectra by searching against animal taxonomy in the Swiss-Prot databases for exact matches using the MASCOT search program (http://www.matrixscience.com; Hirosawa et al., 1993). The mass tolerance of both precursor ion and fragment ions was set to 10 ppm and 0.8 Da, respectively. Searches were performed to allow for the carbamidomethylation (C) as fixed modification, and no trypsin as variable modification.

Peptides were considered identified if their Mascot individual ion score was higher than 20 ($p<0.05$).

1.1.2. Results

Previous experiment evidence shows that crude extract of the inflammatory rabbit skins induced by inoculation of vaccinia virus can exert its pharmacological effect on analgesia. However, the protein concentrations in these extracts were extremely low and below the detection limit, which demonstrated that the protein-level agent hardly played a crucial role in analgesia. To gain an insight into which kind of components were involved in this effect, we employed a proteomic approach to determine the differences in the mass-to-charge ratios (m/z) by using nano LC-MS/MS. The mass spectral patterns of protein fragments generated with or without trypsin digestion were then used for comparison with those of previously known proteins deposited in databanks to confirm peptides, which can be used for identification of intact proteins (protein ID). Therefore, we can achieve an extensive coverage of peptides by shotgun analysis, elucidate the expression profiles of polypeptides or small peptides and identify sequences as well as the biochemical characterization. A flow chart of the methods used in this work is displayed in FIG. 1. The peptides identified in this work and biochemical characterization are listed in Table 1. The representative peptide peak from MS/MS analysis is detected (FIG. 2), resulting in confident protein identification by MASCOT searching. The MS/MS spectrum of the doubly charged ion m/z 773.3192 is shown. The amino acid sequence DEAQETAVSSHEQD (SEQ ID NO: 2), determined from MS differences in the y- and b-fragment ions series and matched residues 1-14 of rabbit α1-antiproteinase F, is absent in human, mouse as well as bovine α1-antiproteinase F. Although both peptides have different length, they share the same origin from the amino acid sequence of rabbit α1-antiproteinase F.

TABLE 1

Characterization of two small peptides identified by MS/MS spectra from nano LC-MS/MS analysis

| Peptide | Protein identified | pI/Mass, Da |
|---|---|---|
| 1 | DEA-X1 (DEAQETAVSSH) | 4.13/1173.16 |
| 5 | DEA-X5 (DEAQETAVSSHEQD) | 3.83/1545.49 |

1.2. Chemical Properties of the AGC Active Ingredients 1.2.1. Materials and Methods 1) Peptide Synthesis Peptides were synthesized by using first-amino-acid-preloaded Wang resin, N-Fmoc amino acids, and PyBOP through solid phase synthesizer (PS3, Protein Technologies, Inc.). The crudes peptides were purified with RP-18 column by medium pressure liquid chromatography (MPLC) and their purities were confirmed as >95% by high performance liquid chromatography (HPLC) under UV detection at 220 nm wavelength. The characterizations of these peptides were proceeded by MALDI-TOF mass spectrometer (Autoflex III system, Bruker Daltonics) and Nuclear Magnetic Resonance spectroscopy (Varian 400 MHz) prior to further studies. Peptide-5 was also received from Mission Biotech Co. (M. B. Taipei, Taiwan) and presented same analgesic activity with our synthesized one.

2) Stability Test

Peptide-5 was dissolved in series of solution with different pH value and stood for 3 days. Adequate amount of each resulting solution was analyzed by HPLC (Agilent 1100 series) using a Nucleodur Pyramid C18 column (250 mm×4.6 mm, 5 μm) and gradient elution (0 min: 0.1% TFA in $H_2O$; 10 min: 0.1% TFA in MeOH; 15 min: 0.1% TFA in MeOH) with 0.2 mL/min flow. The signals were monitored by UV detector at 220 nm wavelength. The sample collected in the stability test was also analyzed by MALDI-TOF Mass (Bruker Daltonics, Autoflex III) with 2,5-dihydroxybenzoic acid (DHB) as matrix. Furthermore, the portion respond to the signal at 7.8 min were collected and subject to MALDI-MS analysis. Peptide-5 was also prepared 50 μM in PBS and recorded from circular dichroism (Jasco, J-810).

1.2.2. Results

Figure 1:
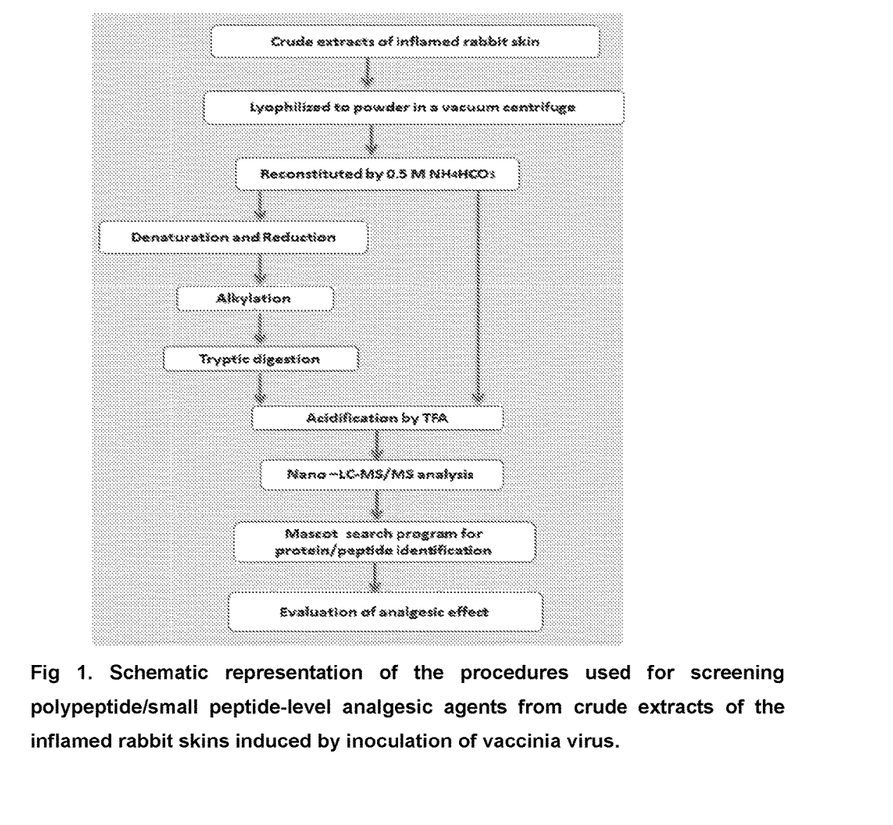
FIG. 1 is a schematic representation of the procedures used for screening polypeptide/small peptide-level analgesic agents from crude extracts of the inflamed rabbit skins induced by inoculation of vaccinia virus.
Figure 2:
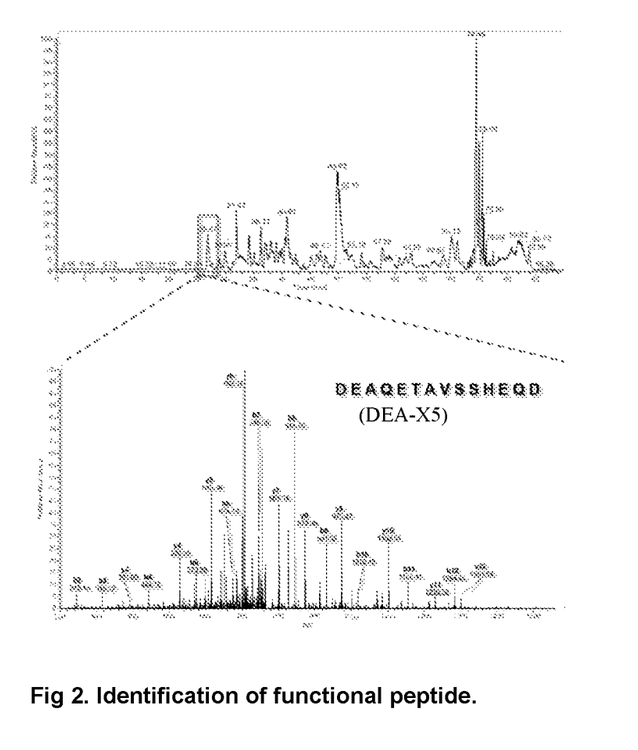
FIG. 2 illustrates the identification of a functional peptide. The MS/MS spectrum of the doubly charged ion m/z 772.745 is shown. One of the amino acid sequences DEAQETAVSSHEQD (SEQ ID NO: 2) shown as an example was determined from MS differences in the y- and b-fragment ions series and matched residues 1-14 of rabbit α1-antiproteinase F.
Figure 3:
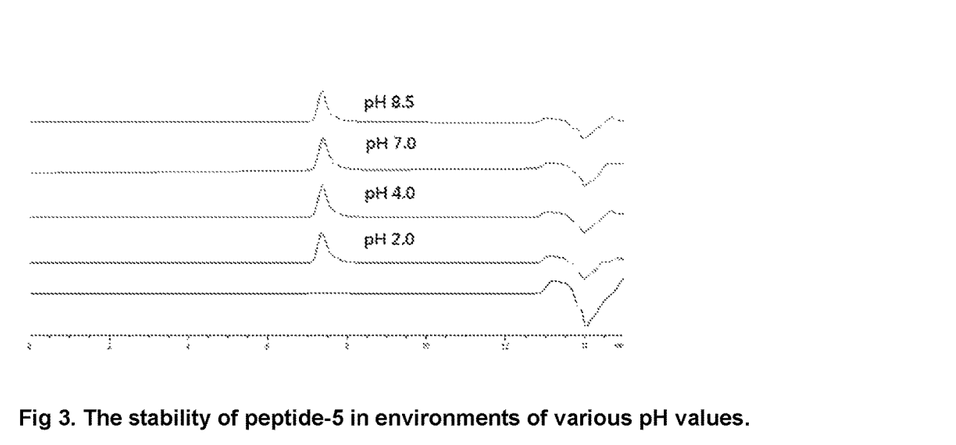
FIG. 3 illustrates the stability of peptide-5 under various pH values.

As shown in FIG. 3, peptide-5 was stood in solution with various pH value (pH 2.0 to 8.5) for 3 day. The resulting solution was analyzed by HPLC and the chromatograms was recorded in UV detector. (Blue line: blank; red line: in pH 2.0; green line: in pH 4.0; pink line: in pH 7.0; black line: in pH 8.5. The retention time of Peptide-5 was 7.8 min.). This indicates that peptide 5 itself is stable, even in a very acidic environment.

Figure 4:
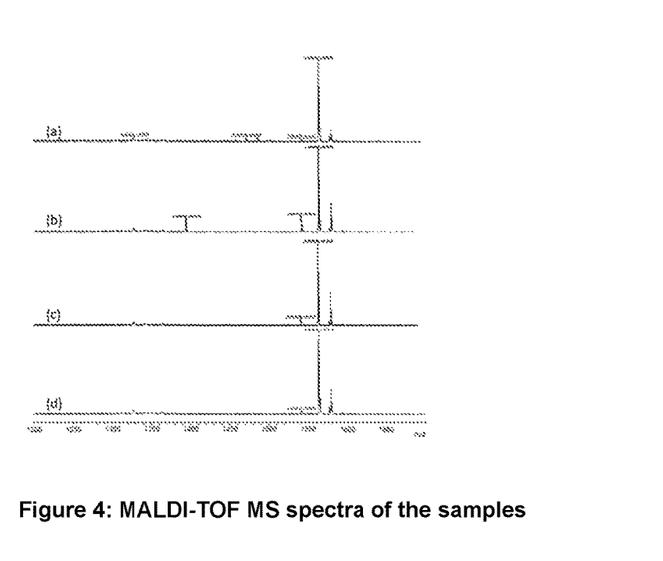
FIG. 4 shows the MALDI-TOF MS spectra of the samples

As shown in FIG. 4, the stability of peptide-5 in solution with various pH value (pH 2.0 to 8.5). The MALDI-TOF MS spectra of the sample respond to the sample in solution with (a) pH 2, (b) pH 4, (c) pH 7 and (d) pH 8.5, respectively.

Figure 5:
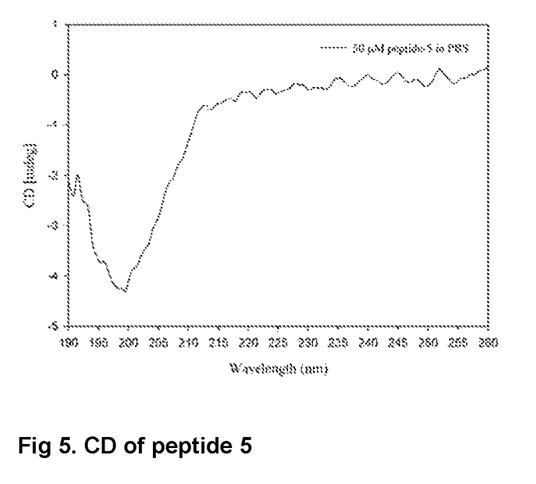
FIG. 5 shows CD (circular dichroism) of peptide 5.

As shown in FIG. 5, the CD of peptide 5 (in 50 μM) revealed that peptide 5 is extremely stable. The CD refers to the differential absorption of left and right circularly polarized light and can be used as an indicator for the secondary structure of a peptide or protein.

The stability of peptide 1 and its CD pattern was similar to those of peptide 5 (data not shown).

1.2.3. Summary

From the experiments above, we confirmed that the peptides isolated from AGC indeed were very stable, at least from the change of pH values in the solvent and the CD patterns. Hence, these peptides could be present in vivo with no significant changes in their structures and sequences.

Example 2

2.1 Protective Effect on Hydrogen Peroxide Treated PC12 Cells 2.1.1 Materials and Methods 1) Isolated Peptides or AGC in PC12 Cell Survival Upon Exposure to $H_2O_2$ PC12 cells, derived from a pheochromocytoma of the rat adrenal medulla that exhibit certain characteristics of neuroganglion cells, were obtained from the Chinese Academy of Medical Sciences, Beijing, China. To examine cell survival upon exposure to $H_2O_2$, PC12 cells were grown to confluence in 96 well plate and the medium was changed to serum-free medium containing 200 μM $H_2O_2$ (final volume 100 μl) for 24 h. In cells receiving treatment, the isolated peptide or AGC was given into wells for 1 h before exposure to $H_2O_2$. After 24 h incubation, 100 μL MTT (final concentration 0.5 mg/ml) was added for additional 4 h incubation, and the cell survival was subsequently assessed by absorbance at 540 nm under a Fluostar microplate reader (BMG, Germany).

2) Statistical Analysis

Data were expressed as mean±standard error (SE) and multiple comparisons were evaluated by the analysis of variance and Neuman-Keuls test. Differences were considered significant at $P<0.05$. Neurological deficit data were evaluated by the nonparametric Mann-Whitney test.

2.1.2 Results

Figure 6:
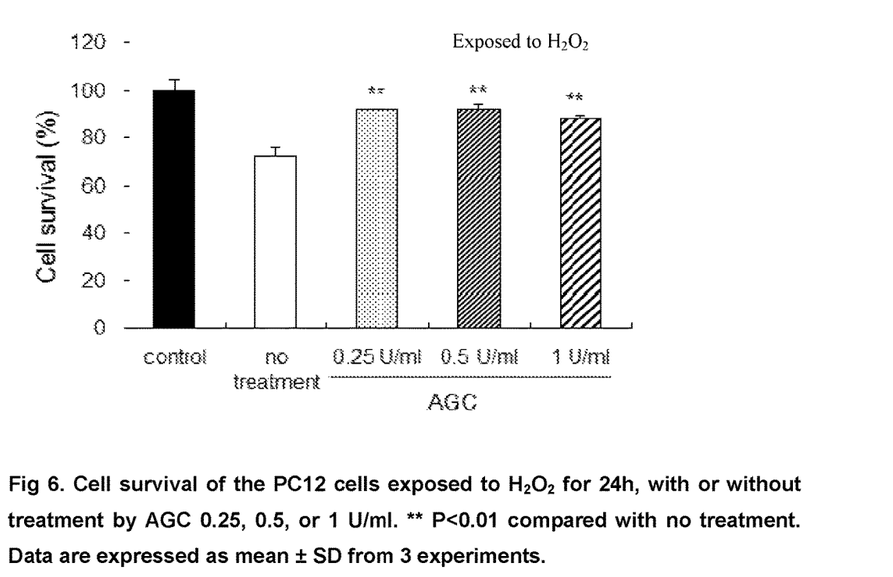
FIG. 6 illustrates cell survival of the PC12 cells exposed to $H_2O_2$ for 24 h, with or without treatment by AGC 0.25, 0.5, or 1 U/ml. ** P<0.01 compared with no treatment. Data are expressed as mean±SD from 3 experiments.
Figure 7:
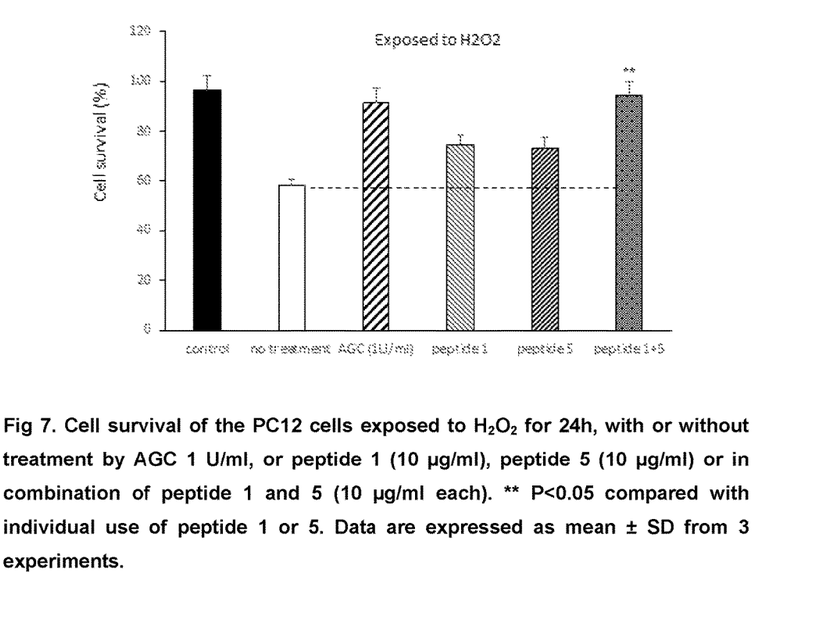
FIG. 7 illustrates cell survival of the PC12 cells exposed to $H_2O_2$ for 24 h, with or without treatment by AGC 1 U/ml, or peptide 1 (10 μg/ml), peptide 5 (10 μg/ml) or in combination of peptide 1 and 5 (10 μg/ml each). ** P<0.05 compared with individual use of peptide 1 or 5. Data are expressed as mean±SD from 3 experiments.

In the experiment, we showed that AGC at 0.25 u/ml, 0.5 u/ml and 1 u/ml have protective effect on the $H_2O_2$-treated neural cells (FIG. 6; $p<0.01$, n=4) and that peptide 1 and peptide 5 (10 ug/ml for each peptide) have a degree of protective effect on the $H_2O_2$-treated neural cells, respectively. Interestingly, when peptide 1 and 5 were combined for treatment, the combined treatment exerted the same degree of protective effect on neural cells as AGC (FIG. 7**; $p<0.01$, n=3).

2.1.3. Summary

From the screening of the effects of protecting cells from the $H_2O_2$-induced cytotoxicity, we provide evidence that (1) AGC indeed possess protective effects against the cytotoxicity derived from exposure of PC12 cells to $H_2O_2$, at concentrations of 0.25-1 U/ml; (2) the peptide 1 and 5 could effectively prevent, at least in part, the $H_2O_2$-induced cytotoxicity of PC12 cells neuronal cells. And, (3) the combinatorial use of peptide 1 and 5 has synergistic effects in protecting PC12 cells from $H_2O_2$-induced cytotoxicity, and the protective effect was as potent as the use of 1 U/ml of AGC.

2.2 Protective Effect on L-Glutamic Acid Treated PC12 Cells 2.2.1 Materials and Methods 1) Effects of Identified Peptides or AGC in PC12 Cell Survival Upon Exposure to L-Glutamic Acid PC12 cells were obtained from the Chinese Academy of Medical Sciences, Beijing, China. To examine cell survival upon exposure to L-glutamic acid, PC12 cells were grown to confluence in 96 well plate in serum-free RPMI-1640. In cells receiving treatment, the identified peptide or AGC at a given dose was put into wells for 1 h before exposure to exposure to L-glutamic acid in the medium of $Mg^{2+}$-free Eagle's medium containing 1 mM L-glutamic acid. After 15-min incubation, medium was changed to serum-free RPMI-1640. After 24 h incubation, 100 μL MTT (final concentration 0.5 mg/ml) was added for additional 4 h incubation, and the cell survival was subsequently assessed by absorbance at 540 nm under a Fluostar microplate reader (BMG Germany).

2) Statistical Analysis

Data were expressed as mean±standard error (SE) and multiple comparisons were evaluated by the analysis of variance and Neuman-Keuls test. Differences were considered significant at $P<0.05$. Neurological deficit data were evaluated by the nonparametric Mann-Whitney test.

2.2.2. Results

Figure 8:
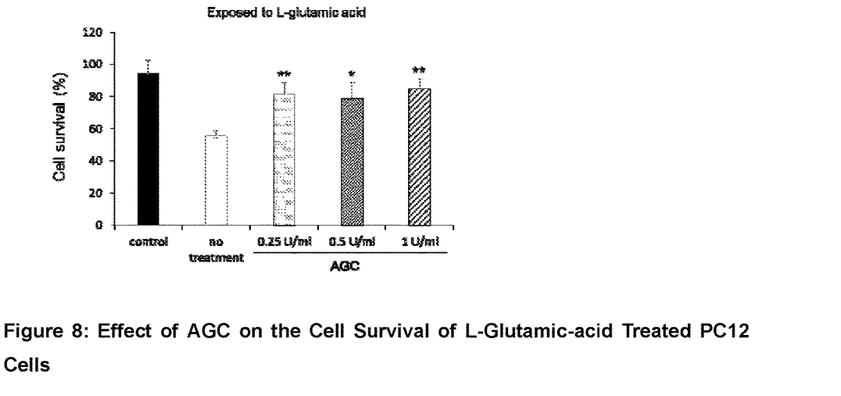
FIG. 8 illustrates the effect of AGC on the cell survival of L-glutamic-acid treated PC12 cells.
Figure 9:
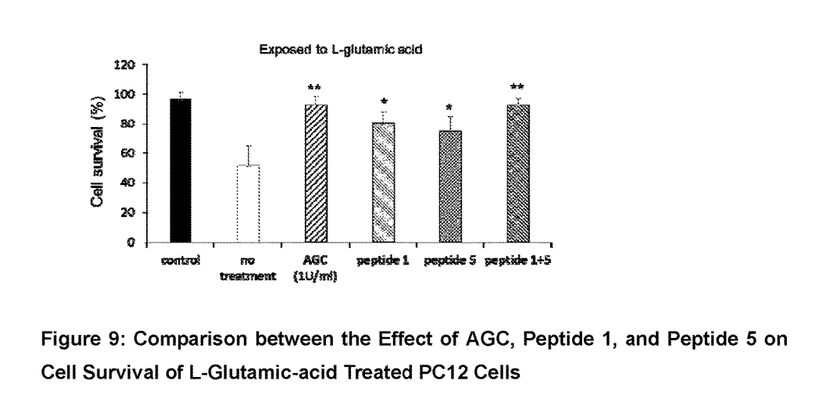
FIG. 9 compares the effect between AGC, peptide 1, and peptide 5 on Cell survival of L-glutamic-acid treated PC12 cells

In this experiment, we showed that different concentrations of AGC (0.25 u/ml, 0.5 u/ml, and 1 u/ml) had positive effect on the cell survival rate of PC12 cells (FIG. 8; *$p<0.05$, $p<0.01$, n=4) and that Peptide 1 and Peptide 5 (10 ug/ml for each peptide) had a degree of protective effect on the L-glutamic-acid-treated PC12 cells, respectively. Interestingly, when peptide 1 and 5 were combined for treatment, the combined treatment exerted the same degree of protective effect on neural cells as AGC (FIG. 9**; *$p<0.05$, **$p<0.01$, n=3).

2.2.3 Summary

Similar to the observation made from exposure of LC12 cells to L-glutamic acid, from the screening of the effects of protecting cells from the L-glutamic acid-induced cytotoxicity, we provide evidence that (1) AGC indeed possess protective effects against the cytotoxicity derived from exposure of PC12 cells to L-glutamic acid, at concentrations of 0.25-1 U/ml; (2) the peptide 1 and 5 could effectively prevent, at least in part, the L-glutamic acid-induced cytotoxicity of PC12 cells neuronal cells. And, (3) the combinatorial use of peptide 1 and 5 has synergistic effects in protecting PC12 cells from L-glutamic acid-induced cytotoxicity, and the protective effect was as potent as the use of 1 U/ml of AGC.

2.3 Protective Effect on Cell Survival of PC12 Cells Under Hypoglycemic, Hypoxic or Hypoglycemic-Hypoxic Conditions 2.3.1 Materials and Methods 1) Effects of AGC and Peptide 1 or 5 in PC12 Cell Survival Cultured in Hypoglycemic, Hypoxic or Hypoglycemic-Hypoxic Conditions PC12 cells were propagated and cultured as described above. For hypoglycemic condition, 125 µM Cobaltous Chloride ($CoCl_2$, Sigma, USA) was added into the culture media when PC12 cells were in monolayer for further 24 h incubation as described. For induction of hypoglycemia, culture media was changed to glucose-free Eagle's medium when PC12 grew to monolayer for additional 24 h incubation. For hypoglycemic and hypoxic conditions, PC12 cells were cultured in glucose-free Eagle's media with addition of 125 µM $CoCl_2$. After 24 h, cells were harvested and subject to MTT assay.

2) Statistical Analysis

Data were expressed as mean±standard error (SE) and multiple comparisons were evaluated by the analysis of variance and Neuman-Keuls test. Differences were considered significant at $P<0.05$. Neurological deficit data were evaluated by the nonparametric Mann-Whitney test.

2.3.2 Results

Figure 10:
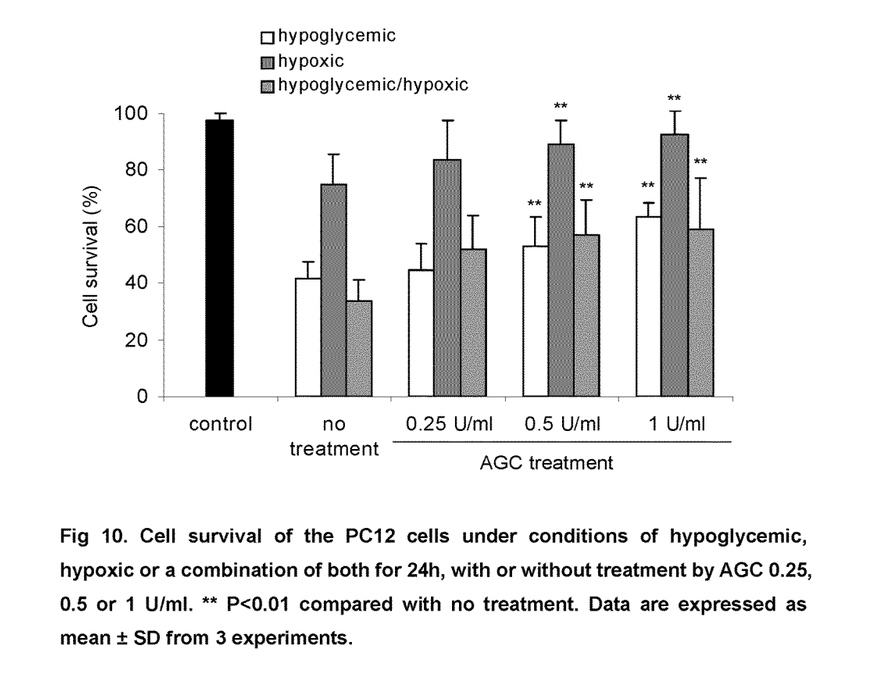
FIG. 10 illustrates cell survival of the PC12 cells under conditions of hypoglycemic, hypoxic or a combination of both for 24 h, with or without treatment by AGC 0.25, 0.5 or 1 U/ml. ** P<0.01 compared with no treatment. Data are expressed as mean±SD from 3 experiments.
Figure 11:
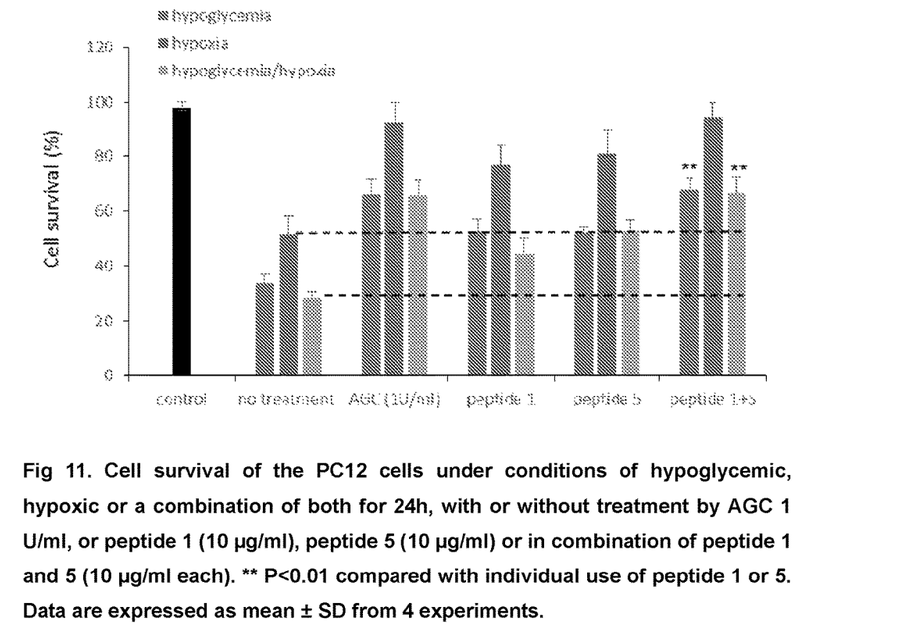
FIG. 11 illustrates cell survival of the PC12 cells under conditions of hypoglycemic, hypoxic or a combination of both for 24 h, with or without treatment by AGC 1 U/ml, or peptide 1 (SEQ ID NO: 1) (10 μg/ml), peptide 5 (SEQ ID NO: 2) (10 μg/ml) or in combination of peptide 1 and 5 (10 μg/ml each). ** P<0.01 compared with individual use of peptide 1 or 5. Data are expressed as mean±SD from 4 experiments.

The experiment showed that AGC (0.5 u/ml, 1 u/ml) had protective effect on PC12 from cell death under hypoglycemic and hypoxic conditions (FIG. 10). Individually, Peptide 1 and Peptide 5 (10 ug/ml for each peptide) had the protective effect as well. However, when these 2 peptides were combined to treat the cells, they exhibited the same degree of effect as AGC (FIG. 11).

2.3.3 Summary

In this experiment, we provide data showing that (1) AGC indeed possess protective effects against the cytotoxicity derived from exposure of PC12 cells to hypoxia, hypoglycemia, or (hypoxia+hypoglycemia), at concentrations of 0.25-1 U/ml; (2) when used individually, peptide 1 or peptide 5 had some protective effect against cell death induced by hypoxia, but no protective effects against the cytotoxicity induced by hypoxia or by (hypoglycemia+hypoglycemia). (3) Nevertheless, when used in combination, peptide 1+5 was protective against the death of PC12 cells exposed to hypoxia, hypoglycemia, or the combination of hypoxia plus hypoglycemia, and the protective effect was with a similar extent when compared to the use of 1 U/ml of AGC.

2.4 In Vivo Distribution of Peptide 1 and 5 after i.v. Injection 2.4.1 Materials and Methods The C57B/L6 mice (6~8 week-old, female) were purchased from National Laboratory Animal Center, Taiwan. For optical imaging, animals were anesthetized by 2% isoflurane gas mixed with oxygen and intravenous injection (i.v.) of Cy5.5-conjugated peptide 1 or Cy5.5-conjugated peptide 5 (35 nmole/per mouse). After administration the mice were placed prone or supine in a dark box and a photographic image was first acquired at low light (exposure time: 5 seconds). At indicated time points after administration of probes, fluorescent signals were obtained using a CCD camera thermoelectrically cooled to −70° C. (Xenogen—IVIS® Spectrum Imaging System, Xenogen Technology). The photon integration period was 1-2 sec. Fluorescent signals were recorded as maximum photos/second/centimeter2/steradian (photon/sec/cm2/sr) and displayed in pseudocolors and superimposed on the photographic image using Xenogen's Living Image software.

2.4.2 Results

Figure 12:
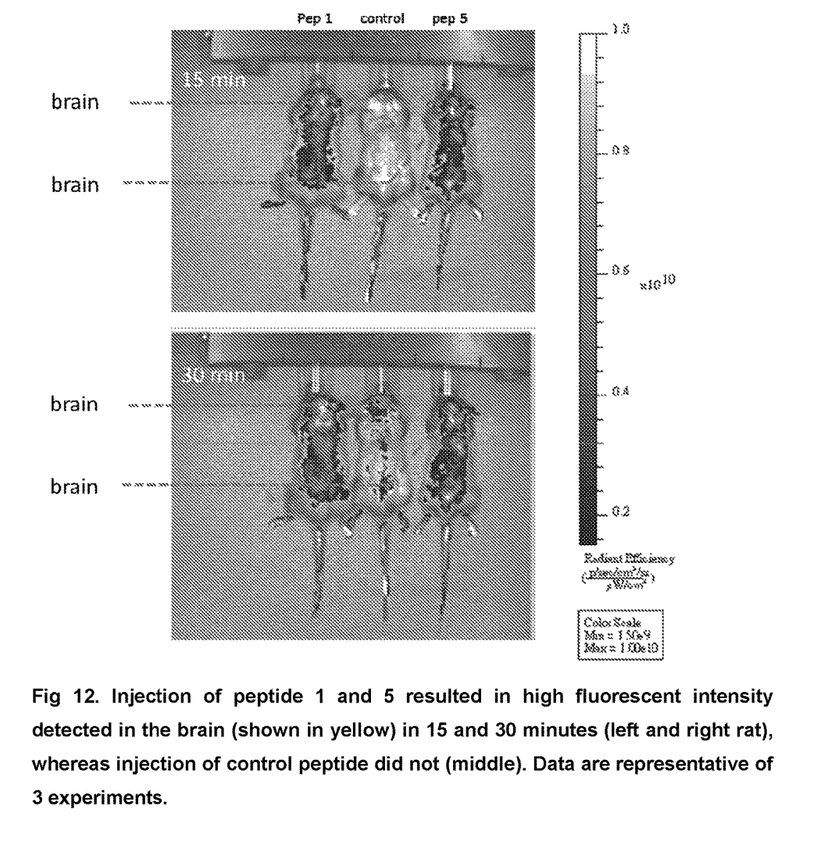
FIG. 12 shows that injection of peptide 1 and 5 resulted in high fluorescent intensity detected in the brain (shown in yellow) in 15 and 30 minutes (left and right rat), whereas injection of control peptide did not (middle). Data are representative of 3 experiments.
Figure 13:
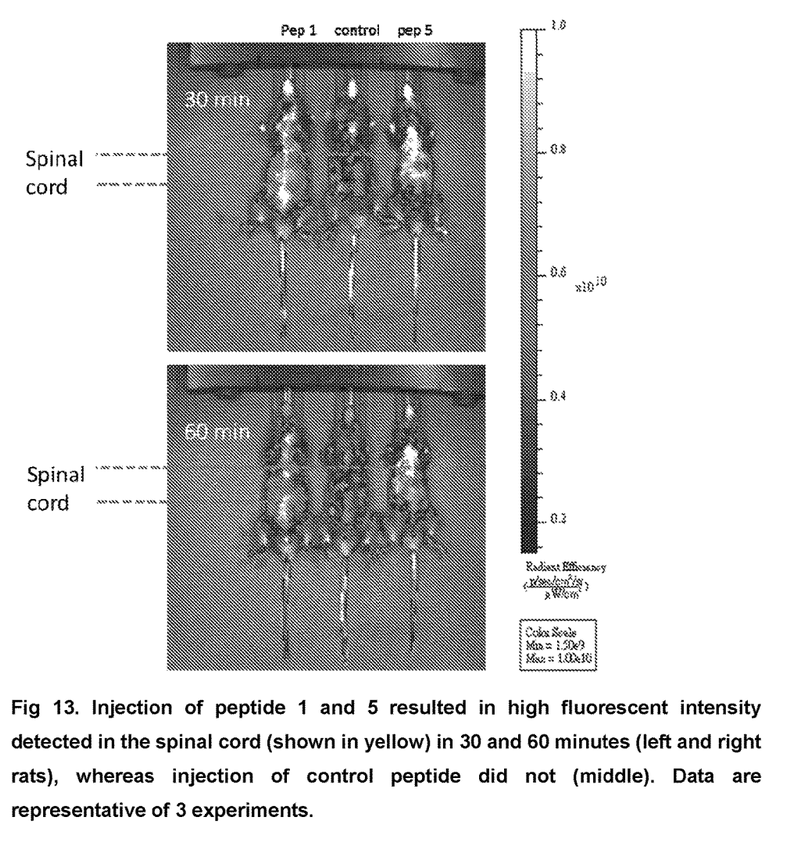
FIG. 13 shows that injection of peptide 1 and 5 resulted in high fluorescent intensity detected in the spinal cord (shown in yellow) in 30 and 60 minutes (left and right rats), whereas injection of control peptide did not (middle). Data are representative of 3 experiments.

Using the in vivo imaging system (IVIS; Perkin Elmer, USA), we can observed that distribution of the 2 peptides injected to the mice through i.v. (FIG. 12). Fifteen minutes after i.v. injection to mice, Peptide 1 and Peptide 5 passed through the blood-brain barrier and reached to the brain. It was observed that the peptides went to the spinal cord at 30 minutes after injection. The peptides stayed in the mice for 1-4 hours with IVIS observable level. The peptides was metabolized and excreted. Furthermore, in the organs extracted ex vivo, we also detected the present of the peptides.

2.4.3 Summary

We thus confirm that both peptide 1 and 5 could migrate from the peripheral circulation through the blood-brain barrier to the brain and spinal cord, as quickly as 15 to 30 minutes after intraperitoneal administration.

This invention includes all modifications and equivalents of the subject matter recited in the claims appended hereto as permitted by applicable law.

REFERENCES

1. Jiang, B. et al. Incidence and trends of stroke and its subtypes in China: results from three large cities. Stroke; a journal of cerebral circulation 37, 63-68, doi:10.1161/01.STR.0000194955.34820.78 (2006).
2. Nedergaard, M., Goldman, S. A., Desai, S. & Pulsinelli, W. A. Acid-induced death in neurons and glia. J Neurosci 11, 2489-2497 (1991).
3. Magistretti, P. J. Cellular bases of functional brain imaging: insights from neuron-glia metabolic coupling. Brain Res 886, 108-112 (2000).
4. Manev, H., Favaron, M., Guidotti, A. & Costa, E. Delayed increase of Ca2+ influx elicited by glutamate: role in neuronal death. Mol Pharmacol 36, 106-112 (1989).
5. Greene, L. A. & Tischler, A. S. Establishment of a noradrenergic clonal line of rat adrenal pheochromocytoma cells which respond to nerve growth factor. Proc Natl Acad Sci USA 73, 2424-2428 (1976).
6. Khan, S., Liu, S., Stoner, M. & Safe, S. Cobaltous chloride and hypoxia inhibit aryl hydrocarbon receptor-mediated responses in breast cancer cells. Toxicol Appl Pharmacol 223, 28-38 (2007).

The invention claimed is:

1. A method for treating or ameliorating cerebrovascular diseases in a subject, wherein the method comprises administering to the subject an effective amount of one or more peptide comprising an amino acid sequence having at least 70% identity to DEAQETAVSSH (SEQ ID NO: 1).

2. The method of claim 1, wherein the amino acid sequence has at least 75% or more identity to SEQ ID NO: 1.

3. The method of claim 1, wherein the peptide comprises SEQ ID NO: 1 and/or DEAQETAVSSHEQD (SEQ ID NO: 2).

4. The method of claim 1, wherein the peptide consists essentially of SEQ ID NO: 1 and/or SEQ ID NO: 2.

5. The method of claim 1, wherein the peptide comprises at least one amino acid addition, deletion, and/or substitution.

6. The method of claim 5, wherein the amino acid addition, deletion and/or substitution are located at the C-terminal and/or N-terminal.

7. The method of claim 5, wherein the peptide has 1-3 amino acid additions, deletions, and/or substitutions.

8. The method of claim 1, wherein the cerebrovascular diseases are those which lead to damages of the neurological systems with functional deficit.

9. The method of claim 1, wherein the cerebrovascular diseases are selected from the group consisting of: ischemic brain injury or hemorrhage brain damage.

10. The method of claim 1, wherein the cerebrovascular disease is stroke.

11. The method of claim 1, wherein the cerebrovascular diseases are treated or ameliorated by protecting nerve cells.

12. The method of claim 1, wherein the subject is human.

* * * * *

UNITED STATES PATENT AND TRADEMARK OFFICE
CERTIFICATE OF CORRECTION

PATENT NO. : 10,130,676 B2
APPLICATION NO. : 15/566937
DATED : November 20, 2018
INVENTOR(S) : Chen-Lung Lin Page 1 of 1

It is certified that error appears in the above-identified patent and that said Letters Patent is hereby corrected as shown below:

On the Title Page

Column 2, Other Publications, Line 9, delete "Huang" and insert --Huong-- therefor.

In the Specification

Column 1, Line 18, delete "FPCH14160101_US_" and insert --FPCH14160101US_-- therefor.

Column 3, Line 30, delete "samples" and insert --samples.-- therefor.

Column 3, Line 46, delete "cells" and insert --cells.-- therefor.

Column 4, Line 45, delete "5" and insert --5.-- therefor.

Column 5, Line 14, delete "Analgecine)" and insert --Analgecine®-- therefor.

Column 8, Line 4, delete "Neuman-Keuls" and insert --Newman-Keuls-- therefor.

Column 8, Line 46, delete "(BMG" and insert --(BMG,-- therefor.

Column 8, Line 50, delete "Neuman-Keuls" and insert --Newman-Keuls-- therefor.

Column 9, Line 37, delete "Neuman-Keuls" and insert --Newman-Keuls-- therefor.

Column 9, Line 66, delete "C57B/L6" and insert --C57BL/6-- therefor.

Signed and Sealed this
Twenty-sixth Day of February, 2019

Andrei Iancu
*Director of the United States Patent and Trademark Office*